United States Patent
Pfeiffer et al.

(10) Patent No.: US 9,557,280 B2
(45) Date of Patent: Jan. 31, 2017

(54) X-RAY TOMOGRAPHY DEVICE

(75) Inventors: Franz Pfeiffer, Garching (DE); Patrice Creux, Lescar (FR); Gérald Hamon, Pau (FR)

(73) Assignees: TOTAL SA, Courbevoie (FR); UNIVERSITE DE PAU ET DES PAYS DE L'ADOUR, Pau (FR)

( * ) Notice: Subject to any disclaimer, the term of this patent is extended or adjusted under 35 U.S.C. 154(b) by 457 days.

(21) Appl. No.: 14/123,031

(22) PCT Filed: Jun. 1, 2012

(86) PCT No.: PCT/EP2012/060441
§ 371 (c)(1),
(2), (4) Date: Nov. 27, 2013

(87) PCT Pub. No.: WO2012/164092
PCT Pub. Date: Dec. 6, 2012

(65) Prior Publication Data
US 2014/0105353 A1    Apr. 17, 2014

Related U.S. Application Data

(60) Provisional application No. 61/492,273, filed on Jun. 1, 2011, provisional application No. 61/492,268, filed on Jun. 1, 2011.

(51) Int. Cl.
G01N 23/04    (2006.01)

(52) U.S. Cl.
CPC ....... *G01N 23/046* (2013.01); *G01N 2223/419* (2013.01)

(58) Field of Classification Search
CPC . A61B 6/4291; A61B 6/484; G01N 2223/064; G01N 2223/1016; G01N 23/20075; G01N 23/046; G01N 15/08; G01N 2223/419; G21K 2207/005

(Continued)

(56) References Cited

U.S. PATENT DOCUMENTS 4,635,197 A * 1/1987 Vinegar ................ G06T 11/005
                                                    250/361 R
4,688,238 A * 8/1987 Sprunt .................. G01N 23/046
                                                    378/210

(Continued)

FOREIGN PATENT DOCUMENTS

DE    19628675    1/1998
DE    102008011301  9/2009

(Continued)

OTHER PUBLICATIONS

Aragodsky, Vadim et al., "High efficiency x-ray source based on inverse Compton scattering in an optical Bragg structure", *Plasma Physics and Controlled Fusion, IOP Publishing*, vol. 53, No. 1, Dec. 16, 2010, pp. 1-10. Examiner note: the submitted document has the author listed as Vadim Karagodsky, not Aragodsky.

(Continued)

*Primary Examiner* — Wyatt Stoffa
(74) *Attorney, Agent, or Firm* — Patterson Thuente Pedersen, P.A.

(57) ABSTRACT

An X-ray tomography device for providing a 3D image of a sample comprising an X-ray source, a cell, a photon detector and a processing unit. The processing unit computes the 3D image on the basis of the images corresponding to a plurality of cell angles. The device further comprises a first and a second gratings having a grating period lower than 200 nm, and a microscope between the second grating and the detector.

10 Claims, 2 Drawing Sheets

(58) Field of Classification Search
USPC .................................................. 378/16, 19
See application file for complete search history.

(56) References Cited

U.S. PATENT DOCUMENTS

| | | | |
|---|---|---|---|
| 5,164,590 A | 11/1992 | Coles et al. | |
| 5,287,396 A | 2/1994 | Stegehuis | |
| 5,635,138 A | 6/1997 | Amatucci et al. | |
| 5,812,629 A * | 9/1998 | Clauser | A61B 6/032 378/37 |
| 5,892,808 A * | 4/1999 | Goulding | G01N 23/046 378/58 |
| 6,035,015 A | 3/2000 | Ruth et al. | |
| 6,687,333 B2 * | 2/2004 | Carroll | H05G 2/00 378/119 |
| 6,839,402 B2 | 1/2005 | Stabe et al. | |
| 7,050,533 B2 | 5/2006 | Heismann et al. | |
| 7,130,375 B1 | 10/2006 | Yun et al. | |
| 7,684,540 B2 | 3/2010 | Groves et al. | |
| 7,924,973 B2 | 4/2011 | Kottler et al. | |
| 7,945,018 B2 | 5/2011 | Heismann et al. | |
| 8,068,579 B1 * | 11/2011 | Yun | G01N 23/046 378/21 |
| 8,073,099 B2 * | 12/2011 | Niu | A61B 6/00 378/36 |
| 8,565,371 B2 * | 10/2013 | Bredno | A61B 6/032 378/9 |
| 8,755,487 B2 * | 6/2014 | Kaneko | A61B 6/06 378/36 |
| 9,084,528 B2 * | 7/2015 | Geller | A61B 6/00 |
| 2005/0286680 A1 * | 12/2005 | Momose | A61B 6/06 378/62 |
| 2007/0183581 A1 * | 8/2007 | Heismann | A61B 6/00 378/145 |
| 2009/0092227 A1 | 4/2009 | David et al. | |
| 2009/0128230 A1 | 5/2009 | Roh et al. | |
| 2009/0128830 A1 * | 5/2009 | Kottler | G01B 15/025 356/521 |
| 2009/0143885 A1 | 6/2009 | Grant et al. | |
| 2009/0316857 A1 * | 12/2009 | David | A61B 6/484 378/62 |
| 2010/0080341 A1 | 4/2010 | Popescu et al. | |
| 2010/0220834 A1 * | 9/2010 | Heismann | A61B 6/032 378/19 |
| 2010/0301458 A1 * | 12/2010 | Sewell | G03F 7/0035 257/618 |
| 2012/0041679 A1 * | 2/2012 | Stampanoni | A61B 6/00 702/1 |
| 2012/0128119 A1 * | 5/2012 | Notohara | A61B 6/025 378/10 |
| 2012/0236985 A1 * | 9/2012 | Schusser | G21K 1/06 378/16 |
| 2013/0094625 A1 * | 4/2013 | Huang | A61B 6/484 378/6 |
| 2014/0086385 A1 | 3/2014 | Creux et al. | |
| 2014/0112440 A1 * | 4/2014 | David | A61B 6/4035 378/62 |
| 2014/0133623 A1 | 5/2014 | Creux et al. | |

FOREIGN PATENT DOCUMENTS

| | | |
|---|---|---|
| GB | 2 185 144 | 7/1987 |
| GB | 2185114 | 7/1987 |
| WO | WO 2006/131235 | 12/2006 |
| WO | WO2010062839 | 6/2010 |

OTHER PUBLICATIONS

Bech, Martin, "X-ray imaging with a grating interferometer", Ph.D. Thesis, Faculty of Science, University of Copenhagen, May 2009, 121 pages.

Herzen, Julia, "A grating interferometer for materials science imaging at a second-generation synchrotron radiation source", Vom Department Physik der Universitat Hamburg im Jahr 2010 als Disssertation angenommene Arbeit, Ph.D. Thesis, HZG Report Feb. 2011, 102 pages.

International Search Report for International Application No. PCT/EP2012/060441 date of mailing Jul. 23, 2012.

International Search Report for International Application No. PCT/EP2012/060440 date of mailing Jul. 24, 2012.

International Search Report for International Application No. PCT/EP2012/060439 date of mailing Jul. 23, 2012.

Kak et al., "Principles of Computerized Tomographic Imaging", IEEE Press, 1988.

Karagodsky et al., "High Efficiency X-ray Source Based on Inverse Compton Scattering in an Optical Bragg Structure", Plasma Physics and Controlled Fusion, IOP Publishing, vol. 53, No. 1. Published Dec. 16, 2010. © 2011 pp. 1-10.

Meyer, V. et al., "Gas Bubble Nucleation of Extra-Heavy Oils in Porous Media: A New Computerized Tomography Technique and Physical Approach", Society of Petroleum Engineers, SPE-110468-PP, Nov. 11-14, 2007, pp. 1-7.

Sachse, Alexander et al., "Functional silica monoliths with hierarchical uniform porosity as continuous flow catalytic reactors", Microporous and Mesoporous Materials, El Sevier, Oct. 26, 2010, pp. 1-11.

Application and File History for U.S. Appl. No. 14/123,000 filed Nov. 27, 2013 inventors Creux et al., as available on PAIR at www.uspto.gov.

Application and File History for U.S. Appl. No. 14/123,018, filed Nov. 27, 2013 inventors Creux et al., as available on PAIR at www.uspto.gov.

* cited by examiner 1) brine [1]    5) water [4]
2) brine [2]    6) light oil [B]
3) light oil [A]  7) ethanol
4) brine [3]

Absorption contrast 1) brine [1]    5) water [4]
2) brine [2]    6) light oil [B]
3) light oil [A]  7) ethanol
4) brine [3]

Phase contrast

X-RAY TOMOGRAPHY DEVICE

PRIORITY CLAIM

The present application is a National Phase entry of PCT Application No. PCT/EP2012/060441, filed Jun. 1, 2012, which claims priority from U.S. Provisional Patent Application No. 61/492,273, filed Jun. 1, 2011, and U.S. Provisional Patent Application No. 61/492,268, filed Jun. 1, 2011, said applications being hereby incorporated by reference herein in their entirety.

FIELD OF THE INVENTION

The present invention concerns an X-ray tomography device.

BACKGROUND OF THE INVENTION

The present invention concerns an X-ray tomography device adapted to petrophysics application, such as to study the flow of fluids into a porous medium. For example, the aim is to study the multiphase flow of a mix of two or three fluids inside a porous medium: a mix of any two of water, gas and oil or the three of them.

The known X-ray tomography systems are adapted to study the morphology of rock pores, to identify the minerals comprised into the rock sample (the porous medium) or the topology of various fluid phases present in the rock sample under static (ie non flowing) conditions.

Moreover, these known tomography systems are not able to visualize small pores in rocks, at the same time as the various fluids or mix of fluids inside the rock and pores of the rock.

OBJECTS AND SUMMARY OF THE INVENTION

One object of the present invention is to provide an X-ray tomography device that can be used to analyse flow of fluids inside a porous medium, such as a rock sample of a geological formation. It is needed an X-ray tomography device having an improved image resolution and an improved capability to distinguish the fluids inside the porous medium for this field of use.

To this effect, the X-ray tomography device according to the invention is adapted for providing a 3D tomography image of a sample, and it comprises:
- a X-ray source emitting a photon beam in the direction of a beam axis,
- a cell adapted to include a porous sample to be imaged, said cell being situated inside the photon beam and being able to rotate about a cell angle around a cell axis that is substantially perpendicular to the beam axis, and being adapted to enable the porous sample to be flooded by at least one fluid,
- a photon detector receiving a transmitted photon beam that is transmitted through said cell, said photon detector providing at least one acquired image for each angle of a plurality of cell angles, and
- a processing unit that computes the 3D tomography image on the basis of the acquired images corresponding to the plurality of cell angles.

The device further comprises following features:
the device further comprises a first and a second gratings positioned between the cell and the detector, so as the photon detector provides at least a first image corresponding to absorption contrast and a second image corresponding to differential phase contrast, the second grating having a grating period lower than 200 nm, and the device further comprises a microscope between said second grating and the detector, for adapting the transmitted photon beam passing through the first and second gratings to the detector.

Thanks to these features, the X-ray tomography device is able to acquire a plurality of accurate first and second images. The data from first and second images can be combined to better distinguish the material nature of each voxel inside the 3D tomography image.

The 3D tomography image can be segmented into regions comprising single material (fluid), and accurate quantities of each fluid can be calculated.

It is possible to have local and global views of the sample. Therefore, the porous medium and the fluid flow in the porous medium of the sample can be studied at the same time at a large or a reduced scale.

In various embodiments of the X-ray tomography device, one and/or other of the following features may optionally be incorporated.

According to an aspect, the second grating comprises a periodic pattern of gold material between stripes.

According to an aspect, the second grating is manufactured by an extreme ultraviolet lithography process.

According to an aspect, the X-ray source is a monochromatic source, and preferably a compact light source using a collision between a laser beam and an opposing electron beam.

According to an aspect, the processing unit is computing the 3D tomography image during a time period lower than an acquisition length of time used for producing the acquired images corresponding to the plurality of cell angles.

According to an aspect, the cell has a size comprised in the range of 0.3 cm to 20 cm, and preferably in the range of 0.6 cm to 10 cm.

According to an aspect, the cell is made of a material in a list comprising the beryllium, the beryllium alloy, and a carbon-carbon composite.

According to an aspect, the processing unit combines at least the first and second images to compute a 3D tomography image having a spatial resolution smaller than a 3D tomography image generated by only one of said first and second images, or wherein the processing unit combines a first 3D tomography image generated by first images and a second 3D tomography image generated by second tomography images to compute a 3D tomography image having a spatial resolution smaller than any one of the first and second 3D tomography images.

BRIEF DESCRIPTION OF THE DRAWINGS

Other features and advantages of the invention will be apparent from the following detailed description of one of its embodiments given by way of non-limiting example, with reference to the accompanying drawings. In the drawings.

MORE DETAILED DESCRIPTION OF THE DRAWINGS

In the various figures, the same reference numbers indicate identical or similar elements. The direction Z is a vertical direction. A direction X or Y is a horizontal or lateral direction. These are indications for the understanding of the invention.

Figure 1:
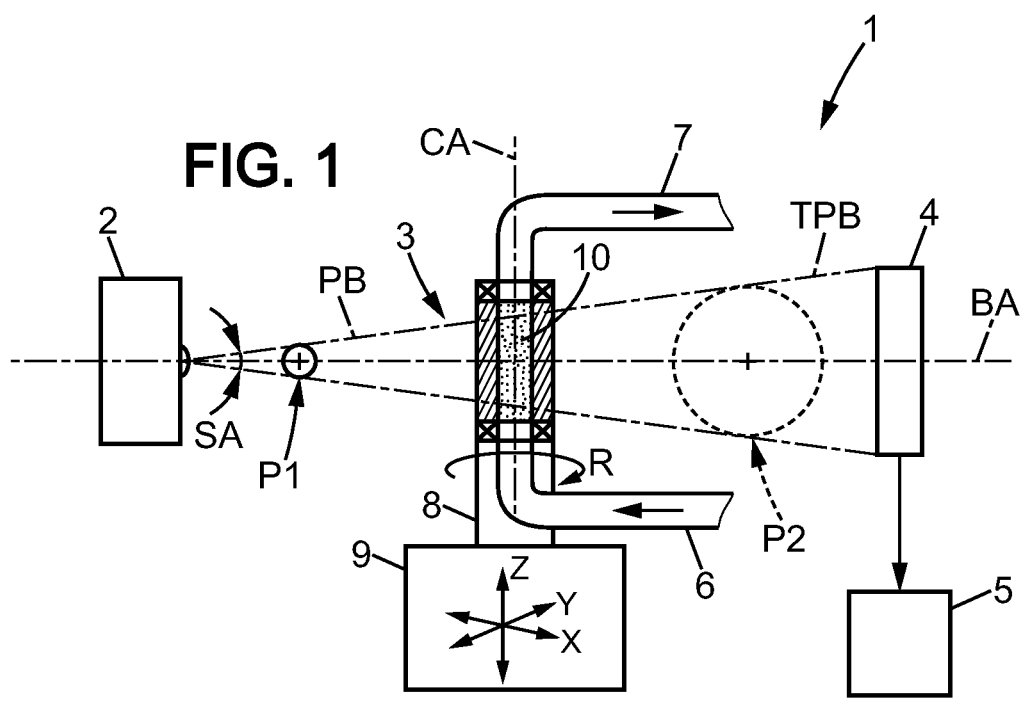
FIG. 1 is a schematic view of a X-ray tomography device according to the invention.

The X-ray tomography device 1 shown on the FIG. 1 comprises:
- a X-ray source 2 emitting a photon beam PB in the direction of a beam axis BA,
- a cell 3 comprising a porous sample 10 to be imaged,
- a photon detector 4 receiving a transmitted photon beam TPB that is transmitted through said cell 3, and
- a processing unit 5 computing the 3D tomography image on the basis of the acquired images provided by the photon detector 4.

The X-ray source 2 may be monochromatic or polychromatic source (synchrotron, lab x-ray source or table top synchrotron), so that the cell may be illuminated with very different levels of brilliance. The polychromatic sources spread their energy into a wide frequency bandwidth. It is possible to filter the photon beam PB to have a quasi-monochromatic photon beam. However, this decreases a lot the photon flux. The monochromatic source concentrates the energy on a very narrow frequency bandwidth. The length of time needed by a detector for acquiring an image is then low therefore non compatible with multiphase flow tracking.

The photon beam PB generated by said X-ray source 2 is a diverging cone beam having a solid angle SA that is wide, and for example higher than 0.1 degree or a few mrad around the beam axis BA. It is possible to illuminate a complete cell having a size of 10 cm at a distance from the X-ray source 2 that is a small distance, for example lower than 25 m, and preferably lower than 10 m. The solid angle SA may be higher than 0.5 degree.

Preferably, the X-ray source is able to emit a photon beam having a high level of energy, for example comprised between 10 and 200 KeV. The photon flux may be higher than $10^8$ photons/s near the photon detector 4, and preferably higher than $10^{11}$ photons/s. The device is then able to image thick cells and thick samples (between 0.3 cm and 10 cm). The X-ray source may have a tuneable X-ray energy level.

For example, the X-ray source 2 may be a compact photon source using collision between a laser beam and an opposing electron beam. Such X-ray source 2 preferentially uses Inverse Compton Effect (Thomson scattering) to generate a natural monochromatic photon beam PB having a high level of energy. The main advantage of such X-ray sources is that they are very compact compared to classical synchrotron devices. Known Table-top synchrotron device using such physical properties are the "Compact Light Source" (CLS) from Lyncean Technologies Inc., but filtering very brilliant polychromatic flux such "Mirrorcle" from Photon Production Lab may produce a quite similar result.

The X-ray source 2 may be tuneable according to the energy level (brilliance) so as to proceed to various experiment above the porous sample.

The cell 3 is situated inside the photon beam PB. The cell position can be controlled via a rotation mean 8 (Z rotation) and a translation mean 9 (XYZ translations).

Thanks to the rotation mean 8, the cell 3 can be rotated around a cell axis CA substantially parallel to axis Z and perpendicular to the X axis, the beam axis BA on FIG. 1. The cell 3 is rotated of a cell angle around the cell axis CA. The detector 4 can then provide images from the cell (sample) from various view angles and the processing unit 5 can compute a 3D tomography image of the sample.

Thanks to the translation mean 9, the cell 3 can be positioned inside the photon beam PB.

The cell 3 can be placed or positioned between a first distance from the source 2 and a second distance from the source 2. The first distance may be short and the cell 3 is close to the X-ray source 2 (see position P1 on FIG. 1). This configuration optimizes the maximal flux in high resolution (stitching mode or local tomography). The second distance is much higher than the first distance, the cell 3 being away from the X-ray source 2. In this configuration, it is possible to illuminate the whole region of interest permitting to easily switch from a global tomography mode to local tomography based on observed changes induced by the multiphase flow. The acquisition time in this last configuration is less performing than the first one but it permits to analyse the sample in interactive mode.

For example, the cylindrical rock sample contained inside the cell 3 has a size comprised in the range of 0.3 cm to 10 cm. The size is preferably in the range 0.6 cm to 3 cm in diameter and in the range of 2 cm to 10 cm in length. The size of the rock sample is chosen big enough to study multiphase transport properties at a scale representative of macroscopic transport properties in the said rock and small enough to enable high resolution tomography of the sample in a length of time that allows imaging the whole sample in less than ten minutes: acquiring the images from the plurality of cell angles within said length of time.

The cell 3 is for example a tube extending along the cell axis CA, said tube receiving the sample of porous medium. The cell 3 comprises an input conduit 6 that input the fluid to the cell 3 and an output conduit 7 that outputs the fluid from the cell. The cell is adapted to be crossed by the fluid.

The X-ray tomography device 1 also comprises hydraulic devices to provide the fluid to the input conduit and to get back this fluid from the output conduit. These hydraulic devices can also add physical conditions to the fluid: temperature, pressure. To this end, these hydraulic devices include a thermal regulator, and a pressure regulator. The sample 10 inside the cell 3 can be tested according to the physical conditions of the geologic formation.

The thermal regulator can heat the sample up to a temperature of 650° Celsius.

The pressure regulator can pressurize the sample up to a pressure of 1000 bars.

The cell 3 is a sort of Hassler cell meeting the requirements of X-ray tomography imaging. The cell 3 is adapted to enable the porous sample 10 to be flooded by one or several fluids under controlled pressure and temperature conditions.

The cell 3 is made of a material that is transparent to the X-ray photon beam. Advantageously, it is made of beryllium, or beryllium alloy such beryllium aluminium alloy, or a carbon-carbon composite.

The photon detector 4 can be tuned to have a sensitivity corresponding to the sample and fluids. Small variations of fluid densities can be therefore detected. Oil and water can be distinguished in the acquired images provided by the photon detector 4 using very fast classical absorption mode, or phase mode or dark field mode.

The photon detector 4 is providing at least one image for each angle of a plurality of cell angles. All these acquired images are taken during a length of time lower than ten minutes for the whole volume to analyse. It is assumed that the state of the sample does not change much during this length of time: the fluid movements inside the porous medium remain very small. All the acquired images from various cell angles are then supposed to represent a unique state of the sample.

Advantageously, the length of time is lower than one minute. The images represent more precisely a unique state of the sample, and the tomography device is acquiring images in real time and stores all these images for the processing unit 5.

The photon detector 4 can be a flat panel, or an X-ray CCD (Charge-Coupled Device) or a CMOS. The photon detector 4 has a high resolution. It is for example a CCD having at least ten megapixels. The acquired images are enough accurate to visualise at the same time (simultaneously) the complete field of view of the sample or very small details inside the sample thanks to a stitching mode or local tomography process. In this way several ways are possible to scan the sample, and the acquired image can be taken in a very short length of time and the acquired image is enough exposed to photon flux to show small details and small variations of densities.

The processing unit 5 is computing the 3D tomography image on the basis of the acquired images corresponding to the plurality of cell angles. Such reconstruction method is known and efficient (fast and providing a very good image quality) benefiting from the quasi parallel approximation. Examples of reconstruction methods can be found in the following document:

A. C. Kak and Malcolm Slaney, *Principles of Computerized Tomographic Imaging*, IEEE Press, 1988.

In the present invention, the processing unit 5 may comprise parallel computing means so that the 3D tomography image can be computed during a very short time period. This high performance for reconstruction time and imaging are mainly due to the quasi parallel beam geometry. The time period can be lower than the length of time for acquiring the images from various cell angles of the sample. The X-ray tomography device is therefore generating real time 3D tomography images, and can visualize a real time movie showing the fluids movements inside the porous medium.

The tomography device 1 may comprise a microscope to obtain high (accurate) resolutions. In that case, the resolution may reach 200 nm of voxel size which is the theoretical limit of microscopes due to Rayleigh criterion.

The tomography device 1 may also comprise a grating based interferometer, situated between the cell 3 and the microscope or the photon detector 4. Such gratings improve the contrast of the acquired images by adding absorption contrast image, phase contrast image and dark field contrast image: materials having similar densities can be distinguished on the acquired images by photon detector 4. In that case, the same resolution than obtained only by the microscope can be obtained.

The gratings, the microscope and the detector 4 compose an optical station of the X-ray tomography device 1.

Figure 2:
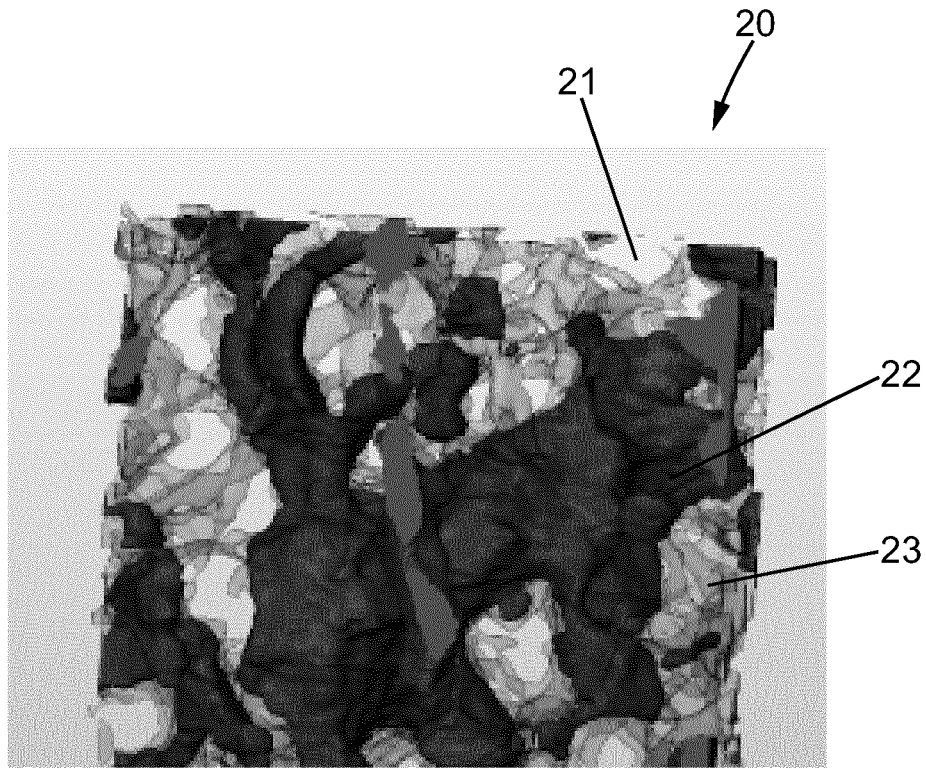
FIG. 2 is an example of a 3D tomography image provided by the device of FIG. 1.

The FIG. 2 is showing an example of a projection of 3D image 20 provided by the X-ray tomography device 1 of the invention. The 3D tomography image comprises various gray levels or various colours, each representing a constituent of the sample. The reference 21 represents the porous medium. The reference 22 represents a first fluid having a first density. The reference 23 represents a second fluid having a second density.

Figure 3:
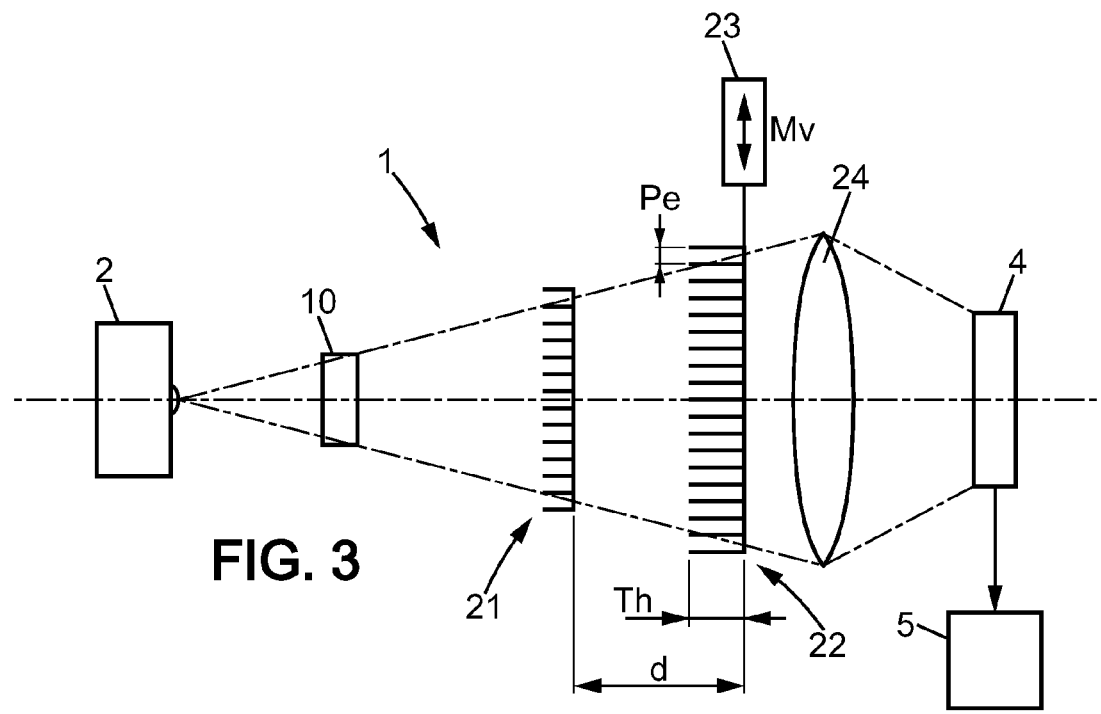
FIG. 3 is another schematic view of the X-ray tomography device according to the invention.

The tomography device 1 according to the invention further comprises a first and second grating (21, 22), and a microscope (24), as represented on FIG. 3.

The first and second gratings (21, 22) are positioned between the cell and the detector. The first grating is a phase grating and the second grating is an analysis grating. These two gratings are parallel to each other, and extend in a plane substantially perpendicular to the beam axis BA. A motor 23 can move the second grating 22 according to a direction perpendicular to the beam axis BA, and relative to the first grating 21. Thanks to this displacement, the detected X-ray beam contribution on the whole volume of interest is coming from the global contributions of the direct absorption beam or a phased beam or a scattered beam, which illuminate the photon detector 4 differently so as to obtain different acquired images of the sample 10.

So, the photon detector 4 is able to provide at least a first image and a second image. The first image is usually called an absorption image. The second image is usually called a differential phase image. The photon detector may also provide a third image, usually called a dark field image. These images are relatively independent to each other. The informations contained in two or three of these images permit to better distinguish the material of each voxel inside the sample 10. It is therefore possible to distinguish materials having same or similar densities.

The refractive index n can be written as a complex value:

$$n = 1 - l + i$$

where
 is an absorption term, linked to the physical density of the material,
 l—is a phase term, linked to the physical density of the material, and also linked to the electron density of said material.

The first and second images give informations of both term of the refractive index, and therefore permit to distinguish materials having the same densities. The third image help to more distinguish the materials (fluids or rock).

The second grating 22 comprises a thickness Th that is adapted to the X-ray energy level, said X-ray energy level being itself adapted to the size and material of the sample 10.

The second grating 22 comprises a grating stripe period Pe that corresponds to the spatial resolution that is desired. The present invention needs a high resolution to get acquired images having small details inside the overall sample volume. The grating period Pe is for example lower than 500 nm, and preferably lower than 200 nm.

The grating can be manufactured by LIGA process (Lithographie, Galvanoformung, Abformung in german language), or preferably by EUVL process (extreme ultraviolet lithography). In case of LIGA process, a metal deposit between the grating stripes can be done during the same process. In case of EUVL process, the grating period can be easily lower than the needed 200 nm limit. Additionally, the grating stripe may be of various materials (not only silicium).

The second grating comprised void that are filed with gold to absorb X-ray periodically. This material can be added inside the void between the grating stripes, for example by a Physical Vapor Deposition (PVD) method.

Thanks to these gratings, having high resolution and high absorbing materials in voids, the X-ray tomography device 1 is able to generate highly contrasted acquired images (absorption, phase or dark field images). The materials inside the sample 10 can therefore be separated from each other. In addition the combination of different 3D tomography images enables to generate after segmentation a final 3D tomography image of very high resolution such that the relative quantities of the materials (rock, fluids) can be precisely calculated, with a precision lower than 3%.

The X-ray tomography device 1 according to the invention further comprises a microscope 24 between the second grating 22 and the photon detector 4. The transmitted photon beam passing through the first and second grating is then focalised to the photon detector 4. All the pixels of the photon detector are used, and the acquired images resolution is also more optimized.

The combination of using different acquired images and using reduced grating periods permits to analyse the 3D tomography images under the pixel or voxel resolution.

For each voxel in the 3D tomography image the quantity of fluid or mix of fluid or rock material can be evaluated. The voxel volume can be lower than 200 nm$^3$, which is a very small volume inside the sample volume.

The quantitative informations that are obtained by the X-ray tomography device of present invention are therefore very accurate. The flow of mix of fluids inside a porous rock sample can be measured and accurately compared to numerical models. The numerical models and hydraulic flow calculation methods can therefore be improved.

Figure 4A:
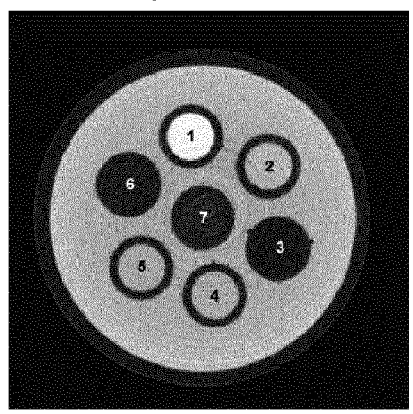
FIGS. 4a and 4b are an example of absorption image and phase image respectively, obtained with the X-ray tomography device of FIGS. 1 and 3 with a test sample.
Figure 4B:
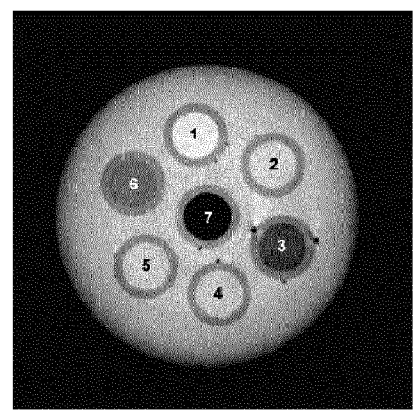

FIGS. 4*a* and 4*b* illustrate the performance obtained with the X-ray tomography device according to the invention, to distinguish various fluids. Both figures show a test sample enclosing seven fluids: The fluids 1, 2 and 4 correspond to brines having various salt concentrations. The fluids 3 and 7 correspond to two different light oils. The fluid 7 is ethanol fluid.

The FIG. 4*a* is the usual absorption image (corresponding to a first image) that is provided by a standard X-ray tomography device. In this image the Fluids 2, 4 and 5 can not cannot be distinguished from each other. The fluids 3, 6 and 7 can not cannot be distinguished from each other. However, said fluids (3, 6 and 7) can be easily distinguished to each other by the image of figure FIG. 4*b* showing a phase image (corresponding to a second image).

The embodiments above are intended to be illustrative and not limiting. Additional embodiments may be within the claims. Although the present invention has been described with reference to particular embodiments, workers skilled in the art will recognize that changes may be made in form and detail without departing from the spirit and scope of the invention.

Various modifications to the invention may be apparent to one of skill in the art upon reading this disclosure. For example, persons of ordinary skill in the relevant art will recognize that the various features described for the different embodiments of the invention can be suitably combined, un-combined, and re-combined with other features, alone, or in different combinations, within the spirit of the invention. Likewise, the various features described above should all be regarded as example embodiments, rather than limitations to the scope or spirit of the invention. Therefore, the above is not contemplated to limit the scope of the present invention.

The invention claimed is:

1. An X-ray tomography device for providing a 3D tomography image of a sample, said device comprising:
    a X-ray source emitting a photon beam in the direction of a beam axis, said photon beam having a solid angle higher than 0.1 degree around said beam axis,
    a cell adapted to include a porous sample to be imaged, said cell being situated inside the photon beam and being able to rotate about a cell angle around a cell axis that is substantially perpendicular to the beam axis, and said cell further including an input conduit to flood the cell by at least one fluid,
    a photon detector receiving a transmitted photon beam that is transmitted through said cell, said photon detector providing at least one acquired image for each angle of a plurality of cell angles, and
    a processing unit that computes the 3D tomography image on the basis of the acquired images corresponding to the plurality of cell angles,
    wherein
    the device further comprises a first and a second gratings positioned between the cell and the detector, so as the photon detector provides at least a first image corresponding to absorption contrast and a second image corresponding to differential phase contrast, the second grating having a grating period lower than 200 nm, and
    the device further comprises a microscope between said second grating and the detector, for adapting the transmitted photon beam passing through the first and second gratings and being focalised to the detector, said detector being an X-ray Charge Coupled Device having a resolution of at least ten megapixels.

2. The X-ray tomography device according to claim 1, wherein the second grating comprises a periodic pattern of gold material between stripes.

3. The X-ray tomography device according to claim 1, wherein the second grating is manufactured by an extreme ultraviolet lithography process.

4. The X-ray tomography device according to claim 1, wherein the X-ray source is a monochromatic source.

5. The X-ray tomography device according to claim 1, wherein the processing unit is computing the 3D tomography image during a time period lower than an acquisition length of time used for producing the acquired images corresponding to all the images in the plurality of cell angles.

6. The X-ray tomography device claim 1, wherein the cell has a size comprised in the range of 0.3 cm to 20 cm.

7. The X-ray tomography device according to claim 1, wherein the cell is comprised of beryllium, beryllium alloy, or a carbon-carbon composite.

8. The X-ray tomography device according to claim 1, wherein the processing unit combines at least the first and second images to compute a 3D tomography image having a spatial resolution smaller than a 3D tomography image generated by only one of said first and second images, or wherein the processing unit combines a first 3D tomography image generated by first images and a second 3D tomography image generated by second tomography images to compute a 3D tomography image having a spatial resolution smaller than any one of the first and second 3D tomography images.

9. The X-ray tomography device according to claim 4 wherein the X-ray source is a compact light source using a collision between a laser beam and an opposing electron beam.

10. The X-ray tomography device claim 6, wherein the cell has a size in the range of 0.6 cm to 10 cm.

* * * * *